United States Patent [19]

McAvinn et al.

[11] 4,295,537

[45] Oct. 20, 1981

[54] SPONGE MEASURING DEVICE

[75] Inventors: James D. McAvinn, Chicago; Arthur R. Meister, Park Ridge; Samuel M. Tucker, Barrington, all of Ill.

[73] Assignee: The Kendall Company, Boston, Mass.

[21] Appl. No.: 132,585

[22] Filed: Mar. 21, 1980

[51] Int. Cl.³ .................. G01G 19/40; G01G 13/14; G01G 19/52; G01G 21/22; A47F 7/08
[52] U.S. Cl. .................................. 177/15; 177/165; 177/245; 177/263; 211/35
[58] Field of Search ............... 177/25, 132, 165, 245, 177/263, 15; 211/35

[56] References Cited

U.S. PATENT DOCUMENTS

| | | | |
|---|---|---|---|
| 1,447,636 | 3/1923 | White | 211/35 UX |
| 2,359,372 | 10/1944 | Leader | 211/35 X |
| 3,367,431 | 2/1968 | Baker | 177/245 X |
| 3,749,237 | 7/1973 | Dorton | |

Primary Examiner—George H. Miller, Jr.
Attorney, Agent, or Firm—Powell L. Sprunger

[57] ABSTRACT

A device for measuring sponges comprising, a measuring device for indicating the weight of an applied object, a retaining device applied to the measuring device for retaining a plurality of wetted sponges, and a determining device associated with the measuring device for determining the total weight of liquid in the retained sponges.

18 Claims, 8 Drawing Figures

U.S. Patent  Oct. 20, 1981  Sheet 1 of 4  4,295,537
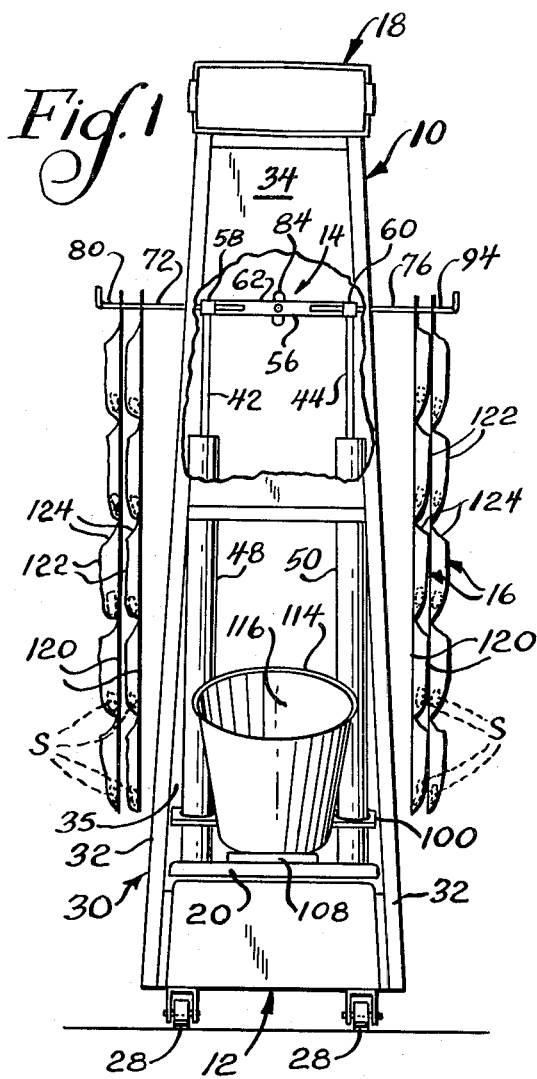
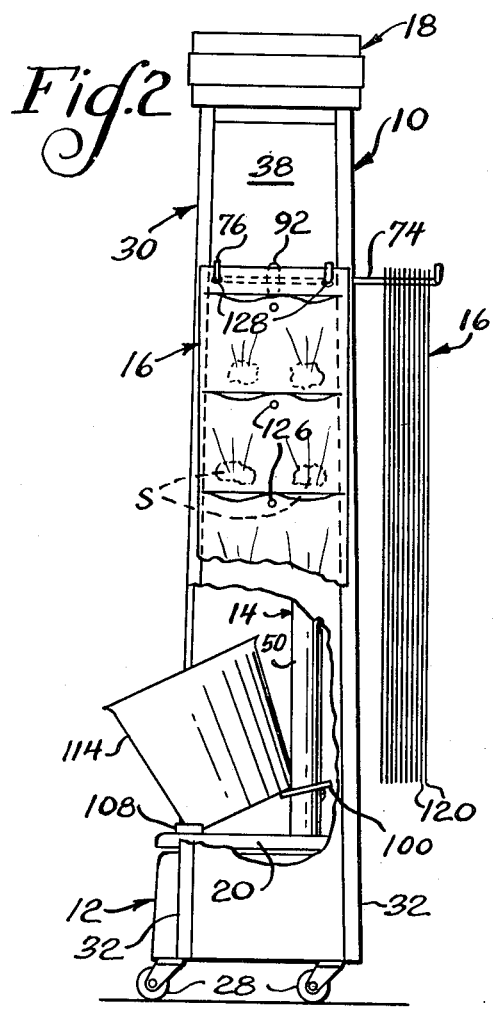
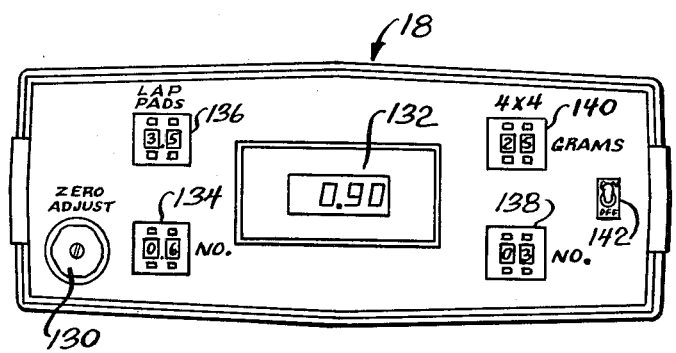

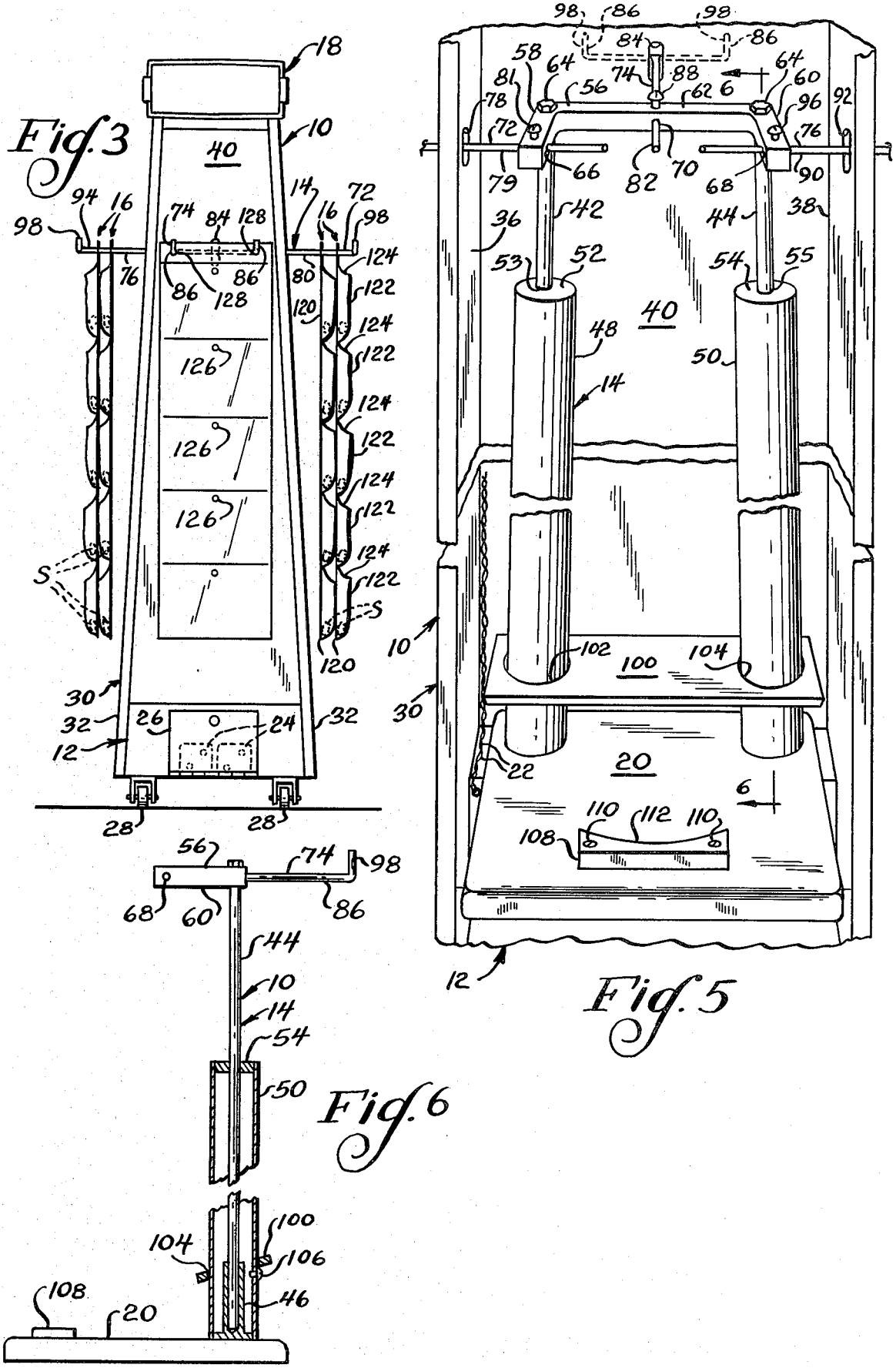

SPONGE MEASURING DEVICE

BACKGROUND OF THE INVENTION

The present invention relates to measuring devices, and more particularly to devices for measuring surgical sponges.

During surgery sponges are frequently used in the incision of the patient to absorb body fluids, such as blood. It is standard practice to count the sponges when they are placed in and removed from the wound to assure that a sponge is not left in the patient when the incision is closed, but the counting of wetted sponges has often proved tedious for the operating personnel. It is also desirable for the surgeon to know the quantity of blood absorbed by the sponges, since the absorbed blood represents a loss of blood by the patient. In certain cases, such as surgery on an infant or during hemorrhages, this knowledge is critical since the patient may require a transfusion in order to restore the blood volume to normal.

SUMMARY OF THE INVENTION

The principal feature of the present invention is the provision of an improved device for measuring sponges.

The device of the present invention comprises, measuring means for indicating the weight of an applied object, and a plurality of retaining assemblies to receive a plurality of wetted sponges, with the retaining assemblies in one form comprising an elongated flexible sheet having a plurality of pockets defining openings to receive the sponges. The device has a support assembly comprising support means applied to the measuring means and means connected to the support means for suspending a plurality of the retaining assemblies. The device also has means for removing the weight of the support assembly and suspended retaining assemblies from the indicated weight of the measuring means, and means for removing the wieght of the retained sponges as nonwetted from the indicated weight of the measuring means.

A feature of the invention is that the device facilitates the collection of wetted sponges.

Another feature of the present invention is that the retaining assemblies facilitate the counting of wetted sponges.

A further feature of the invention is that the device determines the total weight of liquid in the retained sponges.

Thus, another feature of the invention is that the device indicates to the surgeon whether the patient has suffered an abnormal loss of blood.

Still another feature of the invention is that the retaining assemblies can be made from a water soluble material such that the retaining assemblies dissolve during laundry to facilitate reclaiming the laundered sponges for subsequent use.

Further features will become more fully apparent in the following description of the embodiments of this invention and from the appended claims.

DESCRIPTION OF THE DRAWINGS

In the drawings:

FIG. 1 is a fragmentary front elevational view of a sponge measuring device of the present invention;

FIG. 2 is a fragmentary side elevational view of the device of FIG. 1;

FIG. 3 is a rear elevational view of the device of FIG. 1;

FIG. 4 is a front elevational view of a calculating device for the measuring device of FIG. 1;

FIG. 5 is a fragmentary perspective view of the inside of a housing for the device of FIG. 1;

FIG. 6 is a fragmentary sectional view taken substantially as indicated along the line 6—6 of FIG. 5;

DESCRIPTION OF THE PREFERRED EMBODIMENTS

Figure 7A:
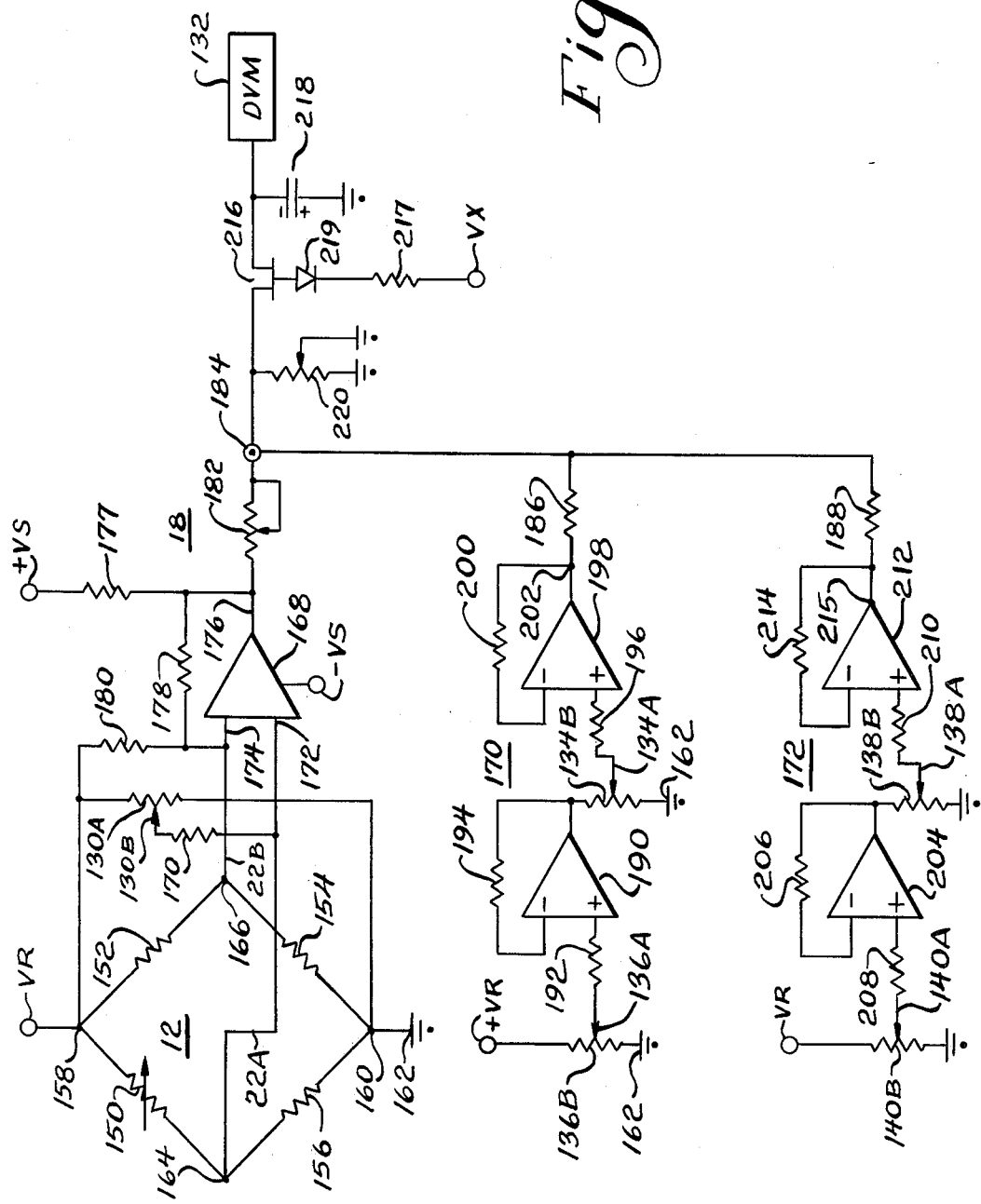
FIG. 7A is a schematic circuit diagram of the calculating device.

Referring now to FIGS. 1-3, 5 and 6, there is shown a sponge measuring device generally designated 10 having a weight measuring device 12, a support assembly 14, a plurality of retaining assemblies 16, and a calculating device 18. The weight measuring device 12 has an upper plate 20 against which loads are applied, and the weight measuring device 12 generates a signal responsive to the applied loads which is indicative of the applied weight. The weight measuring device 12 may be of any suitable type, such as Model 3185 sold by Toledo Scale Company, Toledo, Ohio, or a device disclosed in U.S. Pat. No. 3,770,069 incorporated herein by reference. As shown in FIG. 5, the weight measuring device 12 has a plurality of leads 22 connected to the weight measuring device 12 and extending to the calculating device 18 to carry the signal indicating the weight of the applied load. With reference to FIG. 3, the power supply for the weight measuring device 12 and the calculating device 18 may comprise a pair of rechargeable batteries 24 which are inserted through a rear plate 26 in the weight measuring device 12. Also, as shown in FIGS. 1-3, the device 10 may have a plurality of rollers 28 depending from the weight measuring device 12 to facilitate movement of the device 10 about the operating room.

With reference to FIGS. 1-3, and 5, the device 10 has a housing 30 connected to and extending upwardly from sides of the weight measuring device 12. The housing 30 has a plurality of posts 32 at the corners of the housing 30, and an upper front wall 34 extending between adjacent posts 32 and extending from an upper end of the housing 30 downwardly a portion along the front of the housing 30, such that the upper front wall 34 defines a lower front opening 35. The housing 30 has first and second side walls 36 and 38 extending on opposed sides of the housing 30 between adjacent posts 32 and from the bottom to top of the housing 30 in order to close sides of the housing 30. The housing 30 also has a back wall 40 extending between adjacent posts 32 and extending from the bottom to the top of the housing 30 in order to close the back of the housing 30.

With reference to FIGS. 1-3, 5, and 6, the support assembly 14 has a pair of spaced upright posts or bars 42 and 44 having their lower ends received in attachment members 46 which are secured by suitable means, such as by screws, to the upper surface of the plate 20, such that the weight of the support assembly 14 is applied to the weight measuring device 12. The device 10 has a pair of hollow tubes 48 and 50 received on the posts 42 and 44, respectively, and covering a lower portion of the posts 42 and 44, with the lower end of the tubes 48 and 50 extending around the attachment members 46. The tubes 48 and 50 have upper plates 52 and 54, respectively, covering the upper end of the hollow tubes 48 and 50, and having suitable apertures 53 and 55, respectively, to receive the posts 42 and 44.

The support assembly 14 has a U-shaped support member 56 having a pair of spaced and aligned side bars 58 and 60, and a central bar 62 connecting rear ends of the bars 58 and 60. As shown, the support member 56 is secured to the upper end of the posts 42 and 44 by suitable means, such as by bolts 64, adjacent the juncture of bars 58, 60, and 62. The bar 58 has an aperture 66 extending through a front end portion of the bar 58, the bar 60 has an aperture 68 extending through a front end portion of the bar 60, and the bar 62 has an aperture 70 extending through a central portion of the bar 62.

The support assembly 14 also has a plurality of suspension members 72, 74, and 76 in the general shape of a fork, with each of the suspension members 72, 74, and 76 being similarly shaped. The suspension member 72 has an elongated cylindrical bar 79 slidably received in the aperture 66 of the bar 58, and extending through an elongated slot 78 in the housing sidewall 36, with the suspension member 72 having a pair of outer spaced aligned tines or bars 80 located outside the housing in a configuration with the tines 80 disposed generally parallel to the floor. The position of the bar 79 in the aperture 66 may be adjusted by sliding the bar 79 through the aperture 66, and by setting a bar 79 at a desired location by a suitable screw 81. The suspension member 74 has an elongated cylindrical bar 82 slidably received in the aperture 70 of the bar 62, and extending from the bar 62 through an elongated slot 84 in the back wall 40 to the outside of the housing 30, with the suspension member 74 having a pair of outer spaced aligned tines or bars 86 located outside the housing 30 and being disposed generally parallel to the floor. The bar 82 may be adjusted in the aperture 70, and may be secured at a desired position by a suitable screw 88. The suspension member 76 has an elongated cylindrical bar 90 slidably received in the aperture 68 of the bar 60, and extending through an elongated slot 92 in the side wall 38, with the suspension member 76 having a pair of outer spaced aligned tines 94 located outside the housing and being disposed generally parallel to the floor. The location of the bar 90 may be adjusted in the aperture 68, and may be secured in place by a suitable screw 96. As shown, each of the suspension members 72, 74, and 76 have upwardly directed bars 98 at the outer ends of the respective tines 80, 86, and 94.

The support assembly 14 also has an elongated support plate 100 having a pair of spaced bores 102 and 104 to receive the tubes 48 and 50 of the support assembly 14. The plate 100 is supported at a location spaced above the measuring device plate 20 by a pair of retaining screws 106 in the rear portion of the tubes 48 and 50, with the bores 102 and 104 being slightly larger than the tubes 48 and 50, such that the support plate 100 tilts forwardly on the tubes 48 and 50 from the rear screws 106. As shown, the plate 20 of the weight measuring device 12 has a front guide member 108 secured to the upper surface of the plate 20 by a pair of screws 110, with the guide member 108 having an arcuate recess 112 in a rear portion thereof. Thus, a suitable container or bucket 114 may be positioned on the plate 20 with a forward portion of the container 114 received in the guide member recess 112, and with a rear portion of the container 114 supported by the upper plate 100, such that the container 114 is supported in a forward tilted configuration. Thus, a cavity 116 in the container 114 to receive sponges is directed toward the front part of the housing 30 in the opening 35 to permit easy placement of sponges in the container cavity 116. Also, it will be appreciated that the weight of the container 114 is applied to the weight measuring device 12.

The device 10 has a plurality of retaining assemblies 16 comprising an elongated flexible sheet 120 of suitable material, such as plastic, and a plurality of pockets 122 of flexible material, such as plastic, secured to and disposed along the sheet 120, with the pockets 122 defining openings 124 directed toward an upper portion of the sheet 120 to receive sponges S. In a preferred form, an upper central portion of the pockets 122 are releasably secured to the sheet 120 by suitable tacks 126 for a purpose which will be described below. As shown, the sheets 120 of the retaining assemblies 16 have a pair of upper spaced apertures 128 to receive the spaced tines 80, 86, and 94 of the suspension members 72, 74, and 76, respectively. Thus, the retaining assemblies 16 may be readily placed on and removed from the suspension members 72, 74, and 76.

In a preferred form, the sheets 120 and pockets 122 of the retaining assemblies 16 are made from a water soluble material, such as polyvinyl alcohol. After the soiled wetted sponges S are placed in the retaining assemblies 16, the retaining assemblies 16 may be placed in a washer with the sponges in the pockets 122, such that the retaining assemblies 16 dissolve in the water during laundry to launder the soiled sponges and permit direct access to the laundered sponges, thus eliminating the necessity for removing the sponges from the retaining assemblies 16 prior to laundry.

With reference to FIGS. 1 and 4, the calculating device 18 has an on-off switch 142 of suitable type to permit the operator to connect power to the electrical system of the device 10. The calculating device 18 also has a display register 132 of suitable type which is responsive to the signal from the weight measuring device 12 to indicate the weight of the applied load to the weight measuring device 12. The calculating device 18 has a rotatable knob 130 to permit adjustment of the weight displayed on display register 132 to zero for a purpose which will be described below. The calculating device 18 also has an input register 134 to permit the operator to insert the number of wetted sponges of a first weight which are retained by the device 10. Also, the calculating device 18 has a weight input register 136 associated with the number register 134 to permit the operator to insert the average weight of each nonwetted sponge having the first weight. The calculating device 18 has a second number input register 138 to permit the operator to indicate the number of sponges of a second weight which are retained by the device 10. The calculating device 18 further has a second weight input register 140 to permit the operator to indicate the weight of each nonwetted sponge of the second weight associated with the number input register 138. As will be seen below, the calculating device 18 multiplies the value in register 134 times the value in register 136 and the value in register 138 times the value in register 140 in order to calculate the total dry weight of the retained sponges, and then subtracts the calculated sponge weight from the indicated weight in display register 132.

Figure 7B:
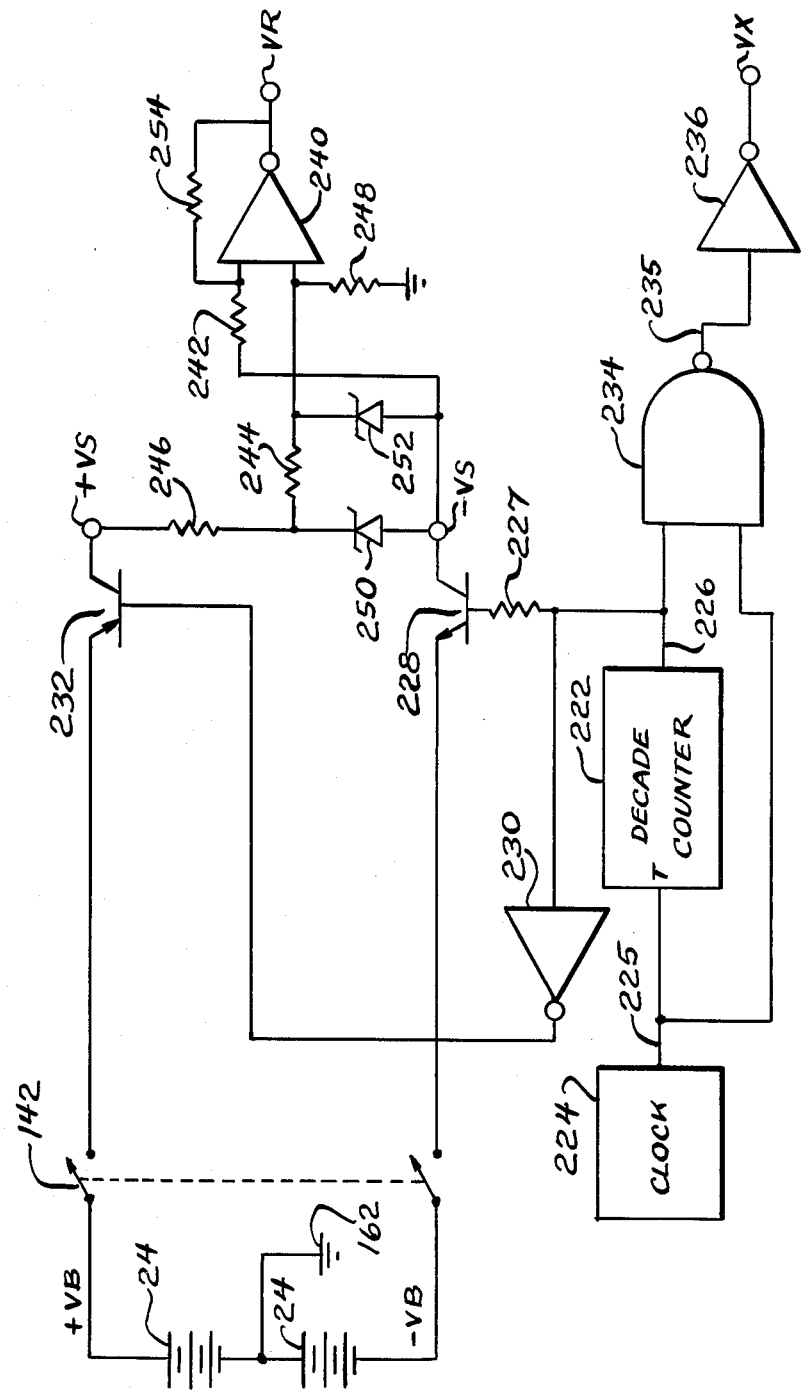
FIG. 7B is a schematic circuit diagram of a power supply switching circuit for the calculating device.

Referring now to FIGS. 7A and 7B, the operation of a preferred form of the weight measuring device 12, the calculating device 18, and the power supply circuits for providing intermittent power supply signals thereto will be described.

As seen in FIG. 7A, the weight measuring device 12 comprises a lab scale of the type employing a load cell resistive element or load cell 150 connected with three other resistors 152, 154 and 156 to form a Wheatstone Bridge circuit. Diametrically opposed power inputs 158 and 160 are respectively coupled to a positive DC reference voltage VR and a ground reference potential 162. The DC voltage VR is a positive voltage developed by the power supply circuit of FIG. 7B, described below. The two output terminals 164 and 166 of the Wheatstone Bridge circuit are coupled through leads 22A and 22B to the calculating device 18. The magnitude of the signal across these two leads is proportional to the weight or load being applied to the load cell 150.

The calculating device 18 includes an operational amplifier 168 for increasing the load cell signals on lines 22A and 22B to a level adequate to drive subsequent circuitry. Device 18 also includes two weight calculators 170 and 172 respectively associated with input registers 134, 136 and 138, 140.

Amplifier 168 has associated with it a rotary potentiometer resistor 130A having a wiper 130B which is controlled by the rotary knob 130, FIG. 4, to adjust the output of amplifier 168 until zero weight is shown on weight register 132 prior to insertion of any sponges into retaining assembly 16. Wiper 130B is connected through a current limiting resistor 170 to lead 22A between output terminal 164 and input 172 of amplifier 168. The potentiometer resistor 130A itself is connected between reference voltage VR and ground reference 162. When potentiometer wiper 130B is adjusted to a position in which the input signal to the input 172 is equal to the input signal to the other input 174 of operational amplifier 168, the signal on output 176 of amplifier 168 will be reduced to zero. This is, of course, done so that the weight of the retaining assembly 16 is not included in the displayed weight.

Amplifier 168 also has associated with it a feedback resistor 178 connected between the output 176 and inverting input 174 which establishes the degree of amplification. Reference voltage VR is applied to input 174 through a bias resistor 180 and the output 176 is coupled to a positive voltage +VS. Positive power supply voltage +VS is periodically applied with a 10% duty cycle to minimize power consumption. Thus, the amplifier 168 provides a signal on its output only 10% of the time. During the on-time of power supply voltages +VS and −VS, the signal on output 176, which represents the total weight being measured, is supplied through a variable current limiting resistor 182 to a summing junction 184. This total weight signal from output 176 has a negative polarity. It is summed with the positive polarity signals from calculators 170 and 172 representing the calculated dry weight to develop a differential signal representative of the weight of only the liquid absorbed by the sponges.

Calculators 170 and 172 are identical in construction except the output resistor 186 for calculator 170 (the laparotomy or large sponge calculator) has a resistance ten times that of output resistor 188 of calculator 172 (the small sponge calculator). For the same electrical input to the calculator 170 and 172, the output amount from resistor 186 of calculator 170 will be one-tenth of the output current from resistor 188 of calculator 172. Accordingly, the smallest unit of weight for register 140 can be expressed in units one-tenth of the smallest weight unit for weight register 136.

Calculator 170 operates as follows. Movement of the weight register 136 causes movement of a wiper blade 136A of a potentiometer resistor 136B connected between ground reference 162 and reference voltage +VR. The magnitude of the signal on the wiper blade 136A represents the average weight entered into the weight register 136. This signal is applied to the noninverting input of operational amplifier 190 through a resistor 192. The amplifier 190 amplifies this weight signal at its noninverting input to a suitable level established by a feedback resistor 194 and applies it to one side of a quantity potentiometer 134B, the other side of which is connected to a ground reference 162.

The quantity multiplicand is then introduced. The potentiometer wiper blade 134A is fixed in a position on potentiometer resistor 134B determined by the quantity setting of the quantity register 134. Thus, a signal is produced on the wiper 134A which has a magnitude proportional to the product of the average weight and the quantity of sponges entered into register 134. This product signal is applied through a resistor 196 to the non-inverting input of an amplifier 198. Amplifier 198 amplifies the signal by a preselected amount determined by the value of a feedback resistor 200, and the amplified product signal is produced on the output 202. The signal on output 202 is then applied through the scaling resistor 186 to summing junction 184.

The calculator 172 operates in an identical fashion as calculator 170 to produce a signal proportional to the total dry weight of the small sponges. The weight register 140 controls a wiper 140A of a potentiometer resistor 140B, and a proportionally amplified weight signal is produced on the output of an amplifier 204. Amplifier 204 and its associated resistors 206 and 208 respectively correspond to amplifier 190 and resistors 194 and 192. This weight signal is then applied to a potentiometer resistor 138B corresponding to potentiometer resistor 134B which has a wiper 138A. The position of wiper 138A is set by quantity register 138. The product signal from wiper 138A is coupled through a resistor 210 to the noninverting input of an amplifier 212 corresponding to amplifier 198. Amplifier 212 has a feedback resistor 214 corresponding to resistor 200. The amplified product signal is produced on output 215 and then coupled to summing junction 184 through resistor 188.

At junction 184 the two amplified product signals of positive polarity are summed with the total weight signal of negative polarity to produce a new signal which has a magnitude equal to the difference between them and is proportional to the weight of the liquid alone in the sponges.

This signal at summing junction 184 is then passed to the display register 132 which is a digital voltmeter through an N-channel field effect transistor or FET 216 which is controlled by a source of voltage VX from the power supply circuit of FIG. 7B. Source VX is coupled to the base of FET 216 through a resistor 217 and a diode 219. Supply voltage VX periodically at an approximate frequency of 3 $H_z$ assumes a positive state only during the first half of each positive pulse of power supply voltage VS to conserve power. During the periods that VX is in an off condition and FET 216 is off, the voltage signal is stored by a capacitor 218 and continues to be displayed as weight by the register 132. A variable resistor 220 provides a means for proportionately adjusting the input level to display register 132.

Referring now to FIG. 7B, the power supply circuit is seen to develop power supply voltage sources +VS, −VS, VR and VX all from rechargeable batteries 24. Batteries 24 are connected to the remainder of the circuitry through on-off switch 142. As seen in FIG. 7B, the junction between the two batteries 24 is coupled to ground reference 162 such that both positive and negative power supply voltages are produced.

All of the supply voltages are applied only intermittently to conserve battery power. This is achieved through a decade counter 222, such as a CD 4017, driven by suitable square wave clock circuit 224. During every tenth clock pulse from clock circuit output 225, a pulse is produced on output 226 of decade counter 222. This pulse is applied through a resistor 227 to the base of a switching NPN transistor 228 to couple battery voltage −VB to supply terminal −VS. Likewise, this pulse is inverted by an inverter 230 and applied to the base of a PNP transistor 232 to couple positive battery voltage +VB to supply terminal +VS during this same time.

The signal on decade counter output 226 is also applied on input of a NAND gate 234 which has as its other input connected to output 225 from clock 224. Accordingly, a negative pulse is produced on the output 235 of NAND gate 234 only during the first half of each positive output pulse on center output 226. This negative pulse on output 235 is inverted by an inverter 236 and appears as a positive pulse on supply terminal VX. Power supply terminal VX, as seen in FIG. 7A, is applied to the base of FET 216 to couple the product signal to the display register 132.

The last power supply voltage VR is developed from the power supply voltages at the terminals +VS and −VS by means of an amplifier 240. Amplifier 240 has one input connected to terminal −VS through a resistor 242 and its other input is connected through resistors 244 and 246 to power supply terminal +VS. A resistor 248 forms a voltage divider with resistor 244 to proportionately reduce the signal applied to the input of amplifier 240 connected to the junction therebetween. Zener diodes 250 and 252 provide regulation, and a feedback resistor 254 establishes the degree of amplification of amplifier 240.

In use, the container 114 may be placed on the weight measuring device 12 through use of the guide member 108 and support plate 100 in a manner as previously described. Also, a plurality of unused retaining assemblies 16 may be positioned on the rear suspension member 74 by inserting the times 86 of the suspension member 74 through the apertures 128 of the sheets 120. Next, the operator utilizes the knob 130 to adjust the display register 132 to a zero value, such that the weight indicated by the register 132 will be null prior to placement of used sponges in the device 10. In this manner, the weight of the unused container 114, the support assembly 14, and the plural unused retaining assemblies 16 is removed from the indicated weight on the display register 132 of the calculating device 18.

The user may then remove a couple of the retaining assemblies 16 from the suspension member 74, and may place one of the retaining assemblies 16 on the suspension member 72 and one of the retaining assemblies 16 on the suspension member 76. As an example when different sizes of sponges are utilized during surgery, the user may rupture the tacks 126 in the retaining assembly 16 on the suspension member 72 to enlarge the pockets 122 of the retaining assembly 16 on the suspension member 72, while the user may leave the tacks 126 in place in the pockets 122 of the retaining assembly 16 on the suspension member 76. Thus, larger sponges, e.g., laparotomy sponges, may be placed in each pocket 122 of the retaining assembly 16 on the suspension member 72, while a pair of smaller sponges, e.g., 4×4 sponges, may be placed in each pocket 122 on opposed sides of the tacks 126 in the retaining assembly 16 on the suspension member 76. Of course, the tacks 126 may be ruptured in the retaining assemblies 16 on both suspension members 72 and 76 if only larger sponges are utilized during surgery, or the tacks 126 in the retaining assemblies 16 may be left intact on both suspension members 72 and 76 if only smaller sponges are utilized during the operation. Alternatively, only one of the suspension members 72 or 76 need be used when only one size of sponge is utilized during surgery.

As surgery progresses and the wetted sponges are removed from the patient's body, they may be placed directly in the retaining assemblies 16 on the suspension members 72 and 76 in accordance with their size, or the wetted sponges may be temporarily placed in the container 114 to permit the operator to later place the sponges in the retaining assemblies 16 when more time is available to the user. When the pockets 122 of a given retaining assembly 16 are completely filled, another retaining assembly 16 is removed from the suspension member 74, and the unused retainined assembly 16 is placed on the appropriate suspension member 72 or 76 to permit placement of further used sponges in the retaining assemblies 16.

When the operation has been completed and all of the wetted sponges have been reclaimed from the patient, the wetted sponges are all placed in the retaining assemblies 16 on the suspension members 72 and 76, including the sponges which may have been initially placed in the container 114. The pockets 122 on the retaining assemblies 16 facilitate counting of the sponges by the user to verify that none of the sponges have been left in the incision of the patient before the incision is closed. Next, the total counted number of larger sponges retained on suspension member 72 is entered on the input register 134 of the calculating device 18, and the average weight of each nonwetted larger sponge is entered on the input register 136 of the calculating device 18. Similarly, the total counted number of smaller sponges on suspension member 76 is entered by the operator on the input register 138 of the calculating device 18, while the average weight of each nonwetted smaller sponge is entered on the input register 140 of the calculating device 18. As previously indicated, the calculating device 18 then calculates the total dry weight of the larger sponges by multiplying the number of sponges entered on register 134 times the average dry sponge weight entered on the register 136, and substractes the total weight of the nonwetted larger sponges from the indicated weight on the display register 132. Similarly, the calculating device 18 calculates the total dry weight of the smaller sponges by multiplying the number of smaller sponges entered on the register 138 times the average dry weight of each smaller sponge entered on the register 140, and subtracts the total dry weight of the smaller sponges from the indicated weight on display register 132. In this manner, the calculating device 18 removes the total weight of the nonwetted sponges from the weight displayed on the register 132.

As previously indicated, the weight of the support assembly 14, the retaining assemblies 16, and the container 114 has already been removed from the indicated weight on the display register 132 by adjusting the displayed weight to zero through use of the knob 130. Since the used retaining assemblies 16 were initially retained on the suspension member 74, removal of the retaining assemblies 16 from the suspension member 74 to the suspension members 72 and 76 does not change the weight contributed by the moved retaining assemblies 16. Thus, the weight remaining, which is displayed on the register 132, is the only weight not removed from the indicated weight, and constitutes the weight of the liquid retained in the wetted sponges. In this manner, the calculating device 18 determines the weight of liquid in the wetted sponges, and indicates the calculated liquid weight on the display register 132 in order that the physician may ascertain the total weight of body fluids, such as blood, lost by the patient and absorbed by the sponges during the operation. Thus, the physician may readily determine whether an abnormal amount of blood has been lost by the patient, and whether the patient may require a transfusion.

The foregoing detailed description is given for clearness of understanding only, and no unnecessary limitations should be understood therefrom, as modifications will be obvious to those skilled in the art.

We claim:

1. A device for measuring sponges, comprising: measuring means for indicating the weight of an applied object; means operatively applied to the measuring means for retaining a plurality of wetted sponges; and electronic means operatively associated with the measuring means for determining the total weight of liquid in said retained sponges.

2. The device of claim 1 wherein the determining means comprises means for removing the total weight of retained sponges as nonwetted from the indicated weight of the measuring means.

3. The device of claim 1 wherein the determining means comprises means for removing the weight of the retaining means and the retained sponges as nonwetted from the indicated weight of the measuring means.

4. The device of claim 1 wherein the retaining means comprises a container having a cavity to receive the sponges.

5. The device of claim 1 wherein the measuring means comprises means for generating a signal responsive to the applied object and indicated of the applied weight.

6. The device of claim 1 wherein the determining means comprises means for removing the weight of the retaining means from the indicated weight of the measuring means.

7. The device of claim 6 wherein the removing means comprises means for setting the indicated weight of the measuring means to a null indication prior to placement of the sponges in the retaining means.

8. A device for measuring sponges, comprising: measuring means for indicating the weight of an applied object; means operatively applied to the measuring means for retaining a plurality of wetted sponges; and means operatively associated with the measuring means for determining the total weight of liquid in said retained sponges, said determining means comprising means for removing the total weight of retained sponges as nonwetted from the indicated weight of the measuring means, said removing means comprising means for indicating the number of retained sponges, means for indicating the weight of each retained nonwetted sponge, means responsive to the number and weight indicating means for calculating the total weight of retained nonwetted sponges, and means responsive to the calculating means for subtracting the calculated weight of nonwetted sponges from the indicated weight of the measuring means.

9. The device of claim 8 wherein the number indicating means has means for indicating the number of a first set of sponges having a first weight and for separately indicating the number of a second set of sponges having a second weight different from the first weight, and in which the weight indicating means has means for separately indicating the differing weights of each nonwetted sponge in the first and second sponge sets.

10. A device for meauring sponges, comprising: measuring means for indicating the weight of an applied object; means operatively applied to the measuring means for retaining a plurality of wetted sponges; and means operatively associated with the measuring means for determining the total weight of liquid in said retained sponges, said retaining means comprising a plurality of retaining assemblies to receive a plurality of sponges, and a support assembly comprising support means applied to the measuring means and means connected to the support means for suspending a plurality of retaining assemblies.

11. The device of claim 10 wherein the suspending means separately suspends a first set of retaining assemblies to receive sponges having a first weight, and a second set of retaining assemblies to receive sponges having a second weight different from said first weight.

12. The device of claim 10 wherein the suspending means separately suspends a first set of unused retaining assemblies, and a second set of used retaining assemblies with received sponges.

13. The device of claim 10 including a closed housing, in which the support means is located inside the housing, and in which the suspending means extends from the support means through a wall of the housing to the outside of the housing.

14. The device of claim 10 wherein the retaining assemblies comprise an elongated sheet of flexible material having a plurality of pockets on the sheet with openings to receive sponges.

15. The device of claim 14 wherein said sheet has a pair of spaced apertures adjacent one end of the sheet, and in which the suspending means comprises a pair of spaced bars received in said apertures.

16. A device to measure sponges, comprising: measuring means for indicating the weight of an applied object; a plurality of retaining assemblies to receive a plurality of wetted sponges; a support assembly comprising support means applied to the measuring means and means connected to the support means for suspending a plurality of retaining assemblies; means for removing the weight of the support assembly and suspended retaining assemblies from the indicated weight of the measuring means; and electronic means for removing the weight of the retained sponges as nonwetted from the indicated weight of the measuring means to determine the total weight of liquid in the retained sponges.

17. A retaining assembly for sponges comprising, an elongated sheet of flexible water soluble material, and a plurality of pockets on the sheet of flexible water soluble material, said pockets defining openings facing toward one end of the sheet to receive sponges.

18. The assembly of claim 17 wherein the material of said sheet and pockets comprises polyvinyl alcohol.

* * * * *